(12) United States Patent
Bogoni et al.

(10) Patent No.: US 10,796,464 B2
(45) Date of Patent: Oct. 6, 2020

(54) SELECTIVE IMAGE RECONSTRUCTION

(71) Applicant: Siemens Healthcare GmbH, Erlangen (DE)

(72) Inventors: Luca Bogoni, Philadelphia, PA (US); Matthias Wolf, Coatesville, PA (US)

(73) Assignee: Siemens Healthcare GmbH, Erlangen (DE)

( * ) Notice: Subject to any disclaimer, the term of this patent is extended or adjusted under 35 U.S.C. 154(b) by 134 days.

(21) Appl. No.: 16/043,290

(22) Filed: Jul. 24, 2018

(65) Prior Publication Data

US 2019/0066343 A1  Feb. 28, 2019

Related U.S. Application Data

(60) Provisional application No. 62/550,034, filed on Aug. 25, 2017, provisional application No. 62/550,030, filed on Aug. 25, 2017.

(51) Int. Cl.
| | |
|---|---|
| *G06K 9/36* | (2006.01) |
| *G06T 11/00* | (2006.01) |
| *G06T 7/11* | (2017.01) |
| *A61B 6/00* | (2006.01) |
| *G06T 3/40* | (2006.01) |

(52) U.S. Cl.
CPC .......... *G06T 11/006* (2013.01); *A61B 6/5205* (2013.01); *G06T 3/4076* (2013.01); *G06T 7/11* (2017.01); *G06T 2207/10081* (2013.01); *G06T 2207/10088* (2013.01); *G06T 2207/10104* (2013.01); *G06T 2207/10108* (2013.01); *G06T 2207/10121* (2013.01); *G06T 2207/10132* (2013.01); *G06T 2211/404* (2013.01)

(58) Field of Classification Search
CPC ....... G06T 11/006; G06T 7/11; G06T 3/4076; G06T 2211/404; G06T 2207/10081; G06T 2207/10108; G06T 2207/10121; G06T 2207/10104; G06T 2207/10132; G06T 2207/10088; A61B 6/5205
See application file for complete search history.

(56) References Cited

U.S. PATENT DOCUMENTS

| | | | | |
|---|---|---|---|---|
| 7,596,284 B2 * | 9/2009 | Samadani | ............. | G06T 3/4007 345/698 |
| 8,315,308 B2 * | 11/2012 | Bao | ...................... | H04N 19/105 375/240.12 |
| 8,319,855 B2 * | 11/2012 | Yang | ................... | H04N 5/23229 348/222.1 |
| 8,331,714 B2 * | 12/2012 | Van Beek | ............. | G06T 3/4007 382/255 |

(Continued)

FOREIGN PATENT DOCUMENTS

EP  1638051 A2  3/2006

*Primary Examiner* — Amir Alavi

(57) ABSTRACT

A framework for selective image reconstruction. In accordance with one aspect, the framework receives at least one first image that is reconstructed based on at least one first reconstruction attribute. At least one region of interest may then be identified in the at least one first image. The framework may selectively reconstruct at least one second image of the region of interest based on at least one second reconstruction attribute, wherein the second reconstruction attribute is different from the first reconstruction attribute. Results may then be generated based on the at least one second image.

16 Claims, 15 Drawing Sheets

(56) References Cited

U.S. PATENT DOCUMENTS

| | | | | |
|---|---|---|---|---|
| 8,374,238 B2* | 2/2013 | Xiong | .................. | H04N 19/172 |
| | | | | 375/240.11 |
| 9,185,437 B2* | 11/2015 | Bivolarsky | .... | H04N 21/234363 |
| 9,648,298 B2* | 5/2017 | Wiegand | .............. | H04N 19/597 |
| 10,110,903 B2* | 10/2018 | Wiegand | ................ | H04N 19/61 |
| 10,250,905 B2* | 4/2019 | Sun | ...................... | H04N 19/149 |
| 2008/0118021 A1 | 5/2008 | Dutta et al. | | |
| 2019/0066343 A1* | 2/2019 | Bogoni | ..................... | G06T 7/11 |

\* cited by examiner

SELECTIVE IMAGE RECONSTRUCTION

CROSS-REFERENCE TO RELATED APPLICATIONS

The present application claims the benefit of U.S. provisional application No. 62/550,034 filed Aug. 25, 2017 and U.S. provisional application No. 62/550,030 filed Aug. 25, 2017, the entire contents of which are herein incorporated by reference.

TECHNICAL FIELD

The present disclosure generally relates to digital medical image data processing, and more particularly to selective reconstruction of images.

BACKGROUND

The field of medical imaging has seen significant advances since the time X-Rays were first used to determine anatomical abnormalities. Medical imaging hardware has progressed from modern machines, such as Magnetic Resonance (MR) imaging scanners, Computed Tomographic (CT) scanners and Positron Emission Tomographic (PET) scanners, to multimodality imaging systems such as PET-CT and PET-MRI systems. Because of large amount of image data generated by such modern medical scanners, there has been and remains a need for developing image processing techniques that can automate some or all of the processes to determine the presence of anatomical abnormalities in scanned medical images.

Digital medical images are reconstructed using raw image data obtained from a scanner, for example, a computerized axial tomography (CAT) scanner, magnetic resonance imaging (MRI), etc. Digital medical images are typically either a two-dimensional ("2D") image made of pixel elements, a three-dimensional ("3D") image made of volume elements ("voxels") or a four-dimensional ("4D") image made of dynamic elements ("doxels"). Such 2D, 3D or 4D images are processed using medical image recognition techniques to determine the presence of anatomical abnormalities or pathologies, such as cysts, tumors, polyps, aneurysms, etc. Given the amount of image data generated by any given image scan, it is preferable that an automatic technique should point out anatomical features in the selected regions of an image to a doctor for further diagnosis of any disease or condition.

Artificial Intelligence (AI) techniques, including Computer-Aided Detection (CAD) techniques, have been used to perform automatic image processing and recognition of structures within a medical image. Recognizing structures of interest within digitized medical images presents multiple challenges. For example, a first concern relates to the accuracy of recognition of structures of interest within an image. A second area of concern is the speed of recognition. Because medical images are an aid for a physician to diagnose a disease or condition, the speed in which an image can be processed and structures within that image recognized can be of the utmost importance to the physician in order to reach an early diagnosis.

Traditional AI systems have focused on detecting or characterizing structures from reconstructed images. While this process has been successful, there is more information in the original raw images which is not accessed. For instance, an AI system may detect or classify a lesion or a structure given a fixed image reconstruction, e.g., 1.25 mm slice-thickness with an axial spatial pixel-resolution of 0.85 mm. While this may be adequate, CT scanners are capable of acquiring image data at substantially higher spatial resolution, which provides a higher discriminative power.

In the above example, a CT thoracic volume may extend 30 cm, thus yielding 240 axial images each containing 512×512 pixels or approximately 126 MB of storage. Currently, larger image matrices of 768×768 pixels or 1024×1024 pixels are allowed by CT imaging systems. Thus, if the above were to be reconstructed at 1.25 mm slice-thickness with a 1024-pixel axial resolution, the storage requirement will be quadrupled to 504 MB. Furthermore, if there was a desire to have an isotropic volume pixel matching the matrix of 1024 (e.g., 0.425), the storage requirement may further increase as the number of axial slices increase. While this is rather large either from storage and processing standpoints, the original raw image data (i.e., minimally processed data from the image sensor) has a much higher resolution and details which, due to matrix limitation alone, cannot be tapped. Reconstruction resolution is achievable up to 0.2 mm, which is roughly four times the original spatial resolution. However, this can lead to axial images of 4 MB per image, and such isotropic volume may yield 1500 slices or roughly 6 GB of storage. Considering that a CT scan is often reconstructed at multiple slice thicknesses and with different kernels, a complete study can easily become too large and impractical. Furthermore, a physician will be overwhelmed by such large amount of data.

SUMMARY

Described herein is a framework for selective image reconstruction. In accordance with one aspect, the framework receives at least one first image that is reconstructed based on at least one first reconstruction attribute. At least one region of interest may then be identified in the at least one first image. The framework may selectively reconstruct at least one second image of the region of interest based on at least one second reconstruction attribute, wherein the second reconstruction attribute is different from the first reconstruction attribute. Results may then be generated based on the at least one second image.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Figure 1:
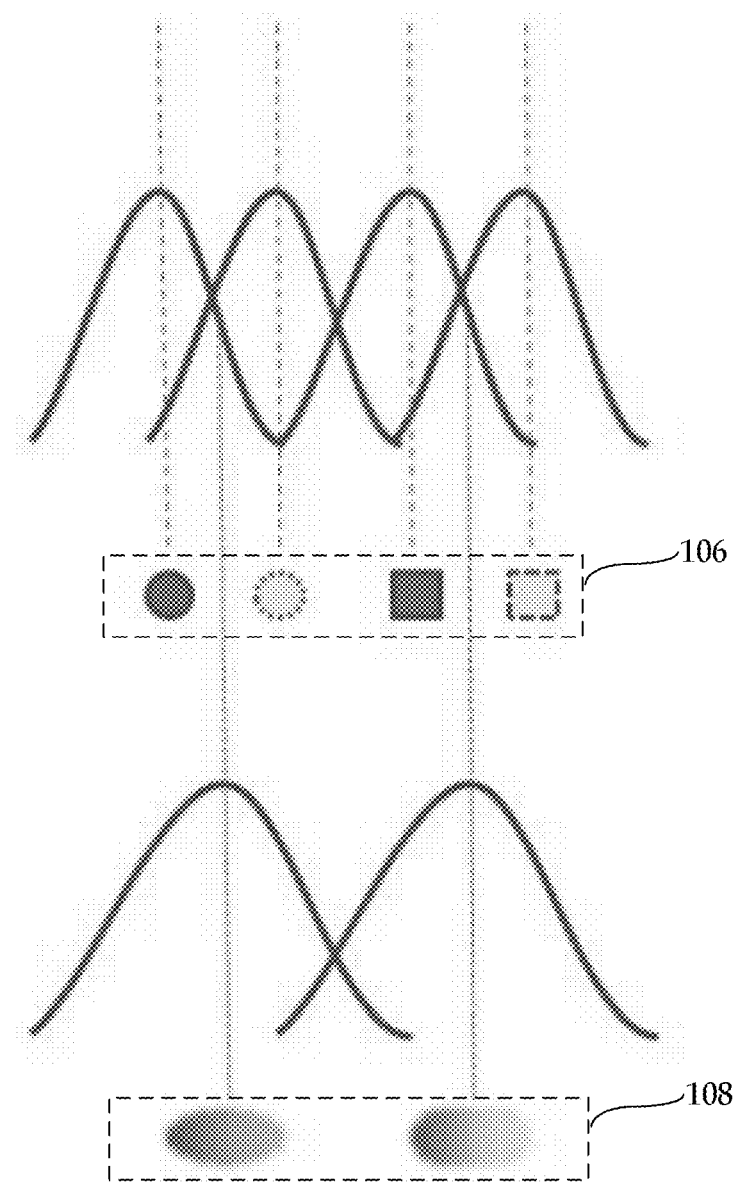
FIG. 1 illustrates reconstruction of adjacent structures at two levels of resolution.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed; on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of an interventional or therapeutic procedure, which may include times when the radiation source is either on or off. From time to time, for convenience of description, CT imaging data (e.g., cone-beam CT imaging data) may be used herein as an exemplary imaging modality. It will be appreciated, however, that data from any type of imaging modality including but not limited to high-resolution computed tomography (HRCT), x-ray radiographs, MRI, PET (positron emission tomography), PET-CT, SPECT, SPECT-CT, MR-PET, 3D ultrasound images or the like may also be used in various implementations.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

As used herein, the term "image" refers to multi-dimensional data composed of discrete image elements (e.g., pixels for 2D images and voxels for 3D images). The image may be, for example, a medical image of a subject collected by computed tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, or a mapping to $R^3$, the present methods are not limited to such images, and can be applied to images of any dimension, e.g., a 2D picture or a 3D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

The terms "pixels" for picture elements, conventionally used with respect to 2D imaging and image display, and "voxels" for volume image elements, often used with respect to 3D imaging, can be used interchangeably. The terms "region of interest", conventionally used with respect to 2D imaging and image display, and "volume of interest", often used with respect to 3D imaging, can be used interchangeably. It should be noted that the 3D volume image itself may be synthesized from image data obtained as pixels on a 2D sensor array and displayed as a 2D image from some angle of view. Thus, 2D image processing and image analysis techniques can be applied to the 3D volume image data. In the description that follows, techniques described as operating upon pixels may alternately be described as operating upon the 3D voxel data that is stored and represented in the form of 2D pixel data for display. In the same way, techniques that operate upon voxel data can also be described as operating upon pixels. In the following description, the variable x is used to indicate a subject image element at a particular spatial location or, alternately considered, a subject pixel. The terms "subject pixel" or "subject voxel" are used to indicate a particular image element as it is operated upon using techniques described herein.

When a physician reviews medical images, these images may already be reconstructed accordingly to specific protocols. In the context of normal anatomy (e.g., lower spine, knees) or specific studies (e.g., heart, liver), the region of interest to be acquired may be predetermined following a scout reconstruction (e.g., CT topogram or MR scan) to determine the pose of the individual in the scanner. In such situation, an initial assessment of the anatomical pose may be made either automatically or manually by the technologist. A targeted protocol may then be initiated to generate a preferred reconstruction.

However, when dealing with localized pathological manifestations or lesions, which are not known prior to clinical review, targeted reconstructions are typically not employed during the image acquisition. This is due to various operational limitations: (1) clinical delay; (2) resource availability; and (3) reconstruction limitations. First, clinical review (radiologist read) may be performed much later after the reconstruction has been completed and the raw image (e.g., CT image) may no longer be available or after the patient has left (e.g., MR or PET images). Second, even when a raw CT image is available, the technologist may not be available to implement other reconstructions. For MR or PET scans, reconstruction is generally not possible after the patient has left. Finally, even when the raw image is available and the technologist is available, the type of reconstructions requested are thinner slices (e.g., 1.0 mm vs. 2.5 mm or 5.0 mm) applied to the complete study (e.g., thorax), or to a portion of the study (e.g., thorax when a scan includes both thorax and abdomen). However, the reconstruction is not easily restricted to a small area within the scan.

In practice, when a radiologist observes a specific lesion or pathology (e.g. one or more lesions in the liver or one or more nodules in the lung), he or she may request additional reconstructions aimed at providing more diagnostic discerning capability. However, while clearly useful, the additional reconstructions provide only limited enhancement; furthermore, while the disambiguation provides a more refined view, this is an improvement primarily with respect to the z-axis. More particularly, such reconstructions are typically refined by including more images (or slices) with a slice thickness of 1.0 mm instead of 2.0 mm. Only partial enhancement is gained axially as the reconstructed series combines less information along the z-axis. Hence, while decreasing slice thickness improves the discrimination, axial resolution is not increased (e.g., matrix size is 512×512). Axial resolution may be increased either by using a larger matrix (e.g. 1024×1024) or "zooming-in" the area of interest.

FIG. 1 illustrates reconstruction of adjacent structures at two levels of resolution. More particularly, adjacent structures 106 are reconstructed at a higher level of resolution with narrower kernel support, while adjacent structures 108 are reconstructed at a lower level of resolution with broader kernel support. Structures 108 not only appear similar at a lower resolution, but major differentiating characteristics are hidden. As the kernel is broadened, information is integrated and differentiation between the structures 108 is blurred. Hence, reconstructions at thinner slices provide only limited insight.

Figure 2:
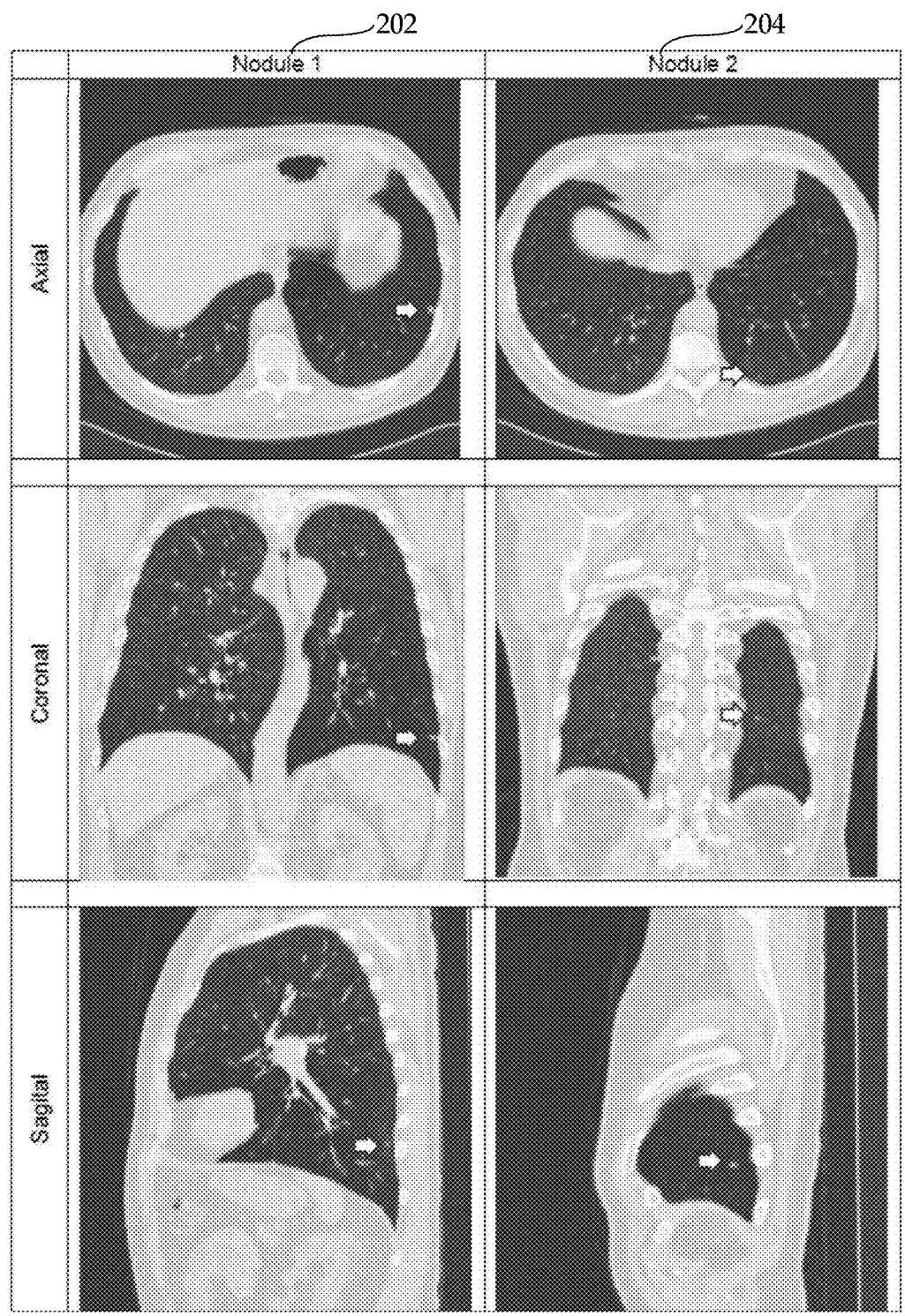
FIG. 2 shows thoracic computed tomographic (CT) images reconstructed at slice thickness of 2.0 mm.

FIG. 2 shows thoracic CT images reconstructed at slice thickness of 2.0 mm. Upon reviewing the case, the radiologist may identify regions of interest (two nodules in this example). Arrows point to specific nodules identified by the radiologist in the three orthogonal views (axial, coronal and sagittal). Column 202 shows the orthogonal views extracted from the volumetric CT image of a first nodule, while column 204 shows the orthogonal views extracted from the volumetric CT image of a second nodule. The original slice thickness of the volumetric CT image is insufficient to diagnose the finding. An additional reconstruction of the complete thorax in thin slices (e.g., at 1.0 mm) may be triggered. While reviewing the additional reconstructed images, the radiologist may use these additional images to zero-in onto the two specific findings to better characterize them. The rest of the reconstruction, while it may prove useful, is usually not explored. The thinner slice reconstructions may also be requested using different kernels (e.g., sharper kernel for thoracic images and smoother kernel for abdominal scans). Hence, a large amount of image data is reconstructed albeit to provide limited disambiguating support for a few structures.

While there may be clinical value in providing additional reconstructions, a radiologist's primary motivation for the additional reconstruction is to gain more clarity on the selected regions of interest. Hence, as proposed in the present framework, providing higher resolution reconstruction of targeted areas of interest addresses this need. In addition, the ability to provide selectively higher resolution images facilitates more precise and accurate quantification (e.g., measurements or segmentation), as will be discussed in the following sections.

Some implementations of the present framework provide an automated mechanism to map an identified region of interest (ROI) (or volume of interest) to an original image (e.g., RAW images) acquired by an imaging device and selectively reconstruct one or more images of the identified region of interest by using one or more different reconstruction attributes (e.g., higher resolution or different kernel). The region of interest may be manually or automatically identified by, for example, a CAD or artificial intelligence (AI) processing. Final results may then be generated based on the one or more reconstructed images.

By precomputing high-resolution image sequences targeted at the specific ROI, the user can better assess whether certain structures previously identified have undergone any change. In fact, not only are high-resolution image sequences clearer, measurements and volumetric assessment based on these reconstructed image sequences may also be more precise or accurate. Additionally, the actual amount of image data that is required to be reconstructed is advantageously reduced by reconstructing only the identified region of interest (ROI). Locations of interest may be automatically mapped to the original images based on user identification. Specific regions of interest may be extracted at the highest resolution based on, for example, previously identified ROI and/or additionally augmented (or replaced) by automatically identified new potential ROI. Increased spatial resolution may be provided along all the orthonormal directions or across preferred axes that naturally align with the structure of interest. This yields a more accurate representation of the underlying structures and volumes.

The present framework advantageously reduces storage requirements by selectively reconstructing only specific regions of interest, instead of capturing the entire width or length of the patient. While image scanners can now yield higher resolution images, these have not been adopted by the clinical institutions. In the CT domain, for instance, conventional axial images have dimensions of 512×512 pixels with spatial resolution per pixel dependent on the Field of View (FoV) of the acquisition. In typical thoracic CT cases, the square pixel dimensions are 0.85 mm as the field of view (FoV) of the image needs to capture the whole patient width (e.g., 43.5 mm). The FoV may be adjusted either manually or automatically. When the patient is rather large, the spatial resolution may further be reduced. Manufacturers have responded by increasing the size of the matrix reconstruction to either 768×768 pixels or even 1024×1024 pixels. In this latter reconstruction, if the number of slices is not increased, the actual storage requirement may quadruple. While storage is not as expensive as it used to be, this may explode the storage requirement per study for only a modest increase in spatial resolution. On the other hand, by selectively reconstructing only specific areas, substantial spatial resolution may be achieved with potentially isotropic reconstructions at 0.33 mm. These and other exemplary features and advantages will be described in more detail herein.

Figure 3:
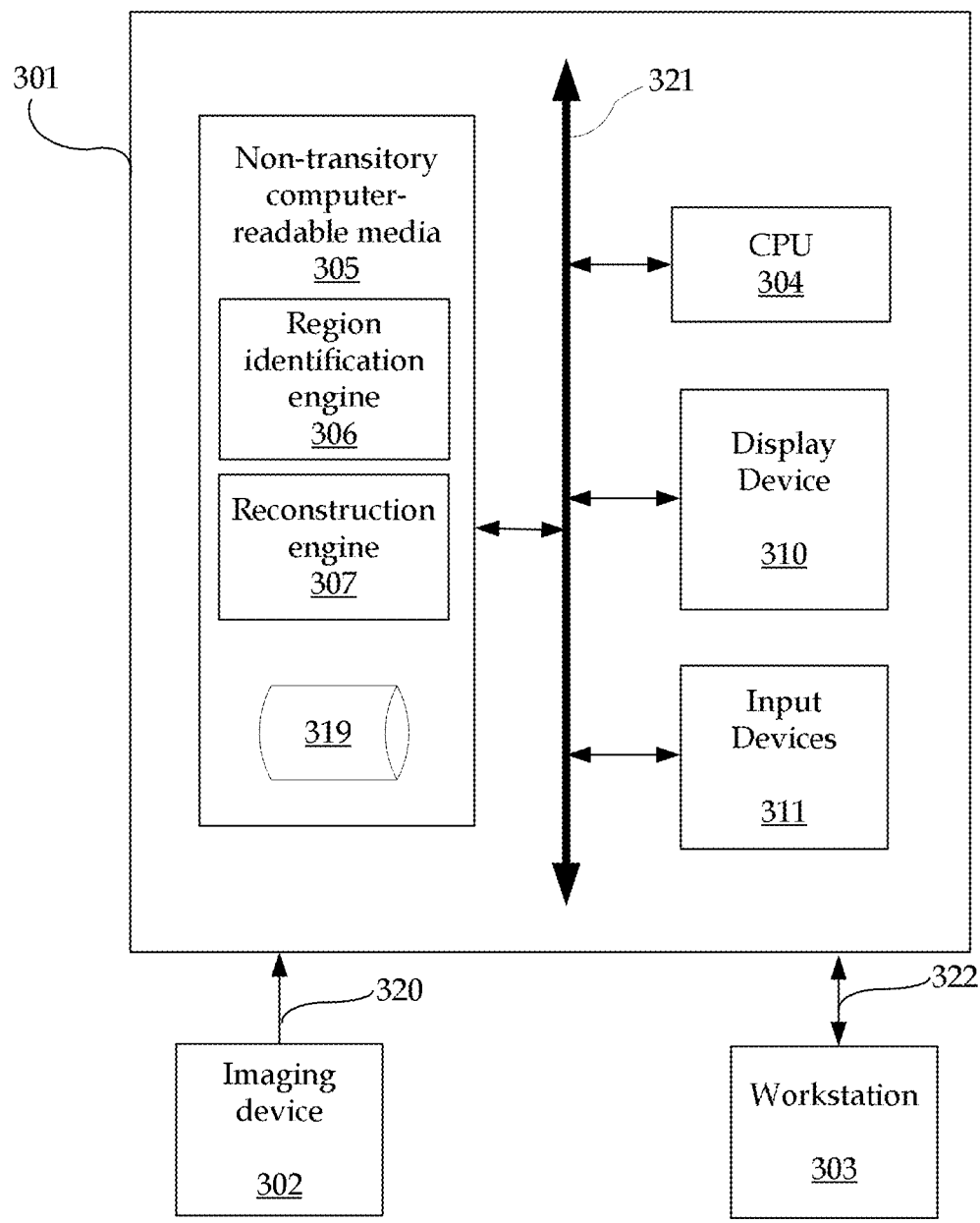
FIG. 3 is a block diagram illustrating an exemplary system.

FIG. 3 is a block diagram illustrating an exemplary system 300. The system 300 includes a computer system 301 for implementing the framework as described herein. In some implementations, computer system 301 operates as a standalone device. In other implementations, computer system 301 may be connected (e.g., using a network) to other machines, such as imaging device 302 and workstation 303. In a networked deployment, computer system 301 may operate in the capacity of a server (e.g., thin-client server), a cloud computing platform, a client user machine in server-client user network environment, or as a peer machine in a peer-to-peer (or distributed) network environment.

In some implementations, computer system 301 includes a processor or central processing unit (CPU) 304 coupled to one or more non-transitory computer-readable media 305 (e.g., computer storage or memory), display device 310 (e.g., monitor) and various input devices 311 (e.g., mouse or keyboard) via an input-output interface 321. Computer system 301 may further include support circuits such as a cache, a power supply, clock circuits and a communications bus. Various other peripheral devices, such as additional data storage devices and printing devices, may also be connected to the computer system 301.

The present technology may be implemented in various forms of hardware, software, firmware, special purpose processors, or a combination thereof, either as part of the microinstruction code or as part of an application program or software product, or a combination thereof, which is executed via the operating system. In some implementations, the techniques described herein are implemented as computer-readable program code tangibly embodied in non-transitory computer-readable media 305. In particular, the present techniques may be implemented by region identification engine 306, reconstruction engine 307 and database 319.

Non-transitory computer-readable media 305 may include random access memory (RAM), read-only memory (ROM), magnetic floppy disk, flash memory, and other types of memories, or a combination thereof. The computer-readable program code is executed by CPU 304 to process medical data retrieved from, for example, database 319. As such, the computer system 301 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 305 may be used for storing a database (or dataset) 319. Such data may also be stored in external storage or other memories. The external storage may be implemented using a database management system (DBMS) managed by the CPU 304 and residing on a memory, such as a hard disk, RAM, or removable media. The external storage may be implemented on one or more additional computer systems. For example, the external storage may include a data warehouse system residing on a separate computer system, a cloud platform or system, a picture archiving and communication system (PACS), or any other hospital, medical institution, medical office, testing facility, pharmacy or other medical patient record storage system.

Imaging device 302 acquires medical images 320 associated with at least one patient. Such medical images 320 may be processed and stored in database 319. Imaging device 302 may be a radiology scanner (e.g., MR scanner) and/or appropriate peripherals (e.g., keyboard and display device) for acquiring, collecting and/or storing such medical images 320.

The workstation 303 may include a computer and appropriate peripherals, such as a keyboard and display device, and can be operated in conjunction with the entire system 300. For example, the workstation 303 may communicate directly or indirectly with the imaging device 302 so that the medical image data acquired by the imaging device 302 can be rendered at the workstation 303 and viewed on a display device. The workstation 303 may also provide other types of medical data 322 of a given patient. The workstation 303 may include a graphical user interface to receive user input via an input device (e.g., keyboard, mouse, touch screen voice or video recognition interface, etc.) to input medical data 322.

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 4:
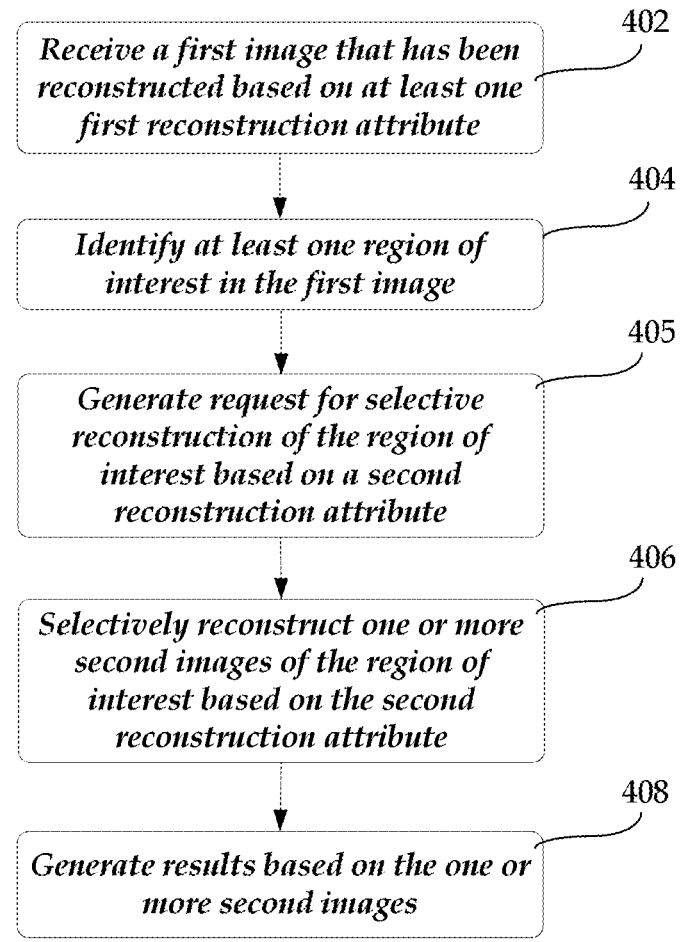
FIG. 4 shows an exemplary method of selective image reconstruction by a computer system.

FIG. 4 shows an exemplary method 400 of selective image reconstruction by a computer system. It should be understood that the steps of the method 400 may be performed in the order shown or a different order. Additional, different, or fewer steps may also be provided. Further, the method 400 may be implemented with the system 301 of FIG. 3, a different system, or a combination thereof.

At 402, region identification engine 306 receives a first image of a structure of interest that has been reconstructed based on at least one first reconstruction attribute. The structure of interest may be an anatomical structure, such as the heart, brain, lungs, thorax, etc. The first image may be a two-dimensional (2D) image slice or a three-dimensional (3D) image volume. The first image may be retrieved from, for example, database 319 and/or reconstructed from raw image data (i.e., minimally processed data) acquired by imaging device 302. The imaging device 302 may acquire the raw image data by using techniques such as high-resolution computed tomography (HRCT), magnetic resonance (MR) imaging, computed tomography (CT), helical CT, X-ray, angiography, positron emission tomography (PET), fluoroscopy, ultrasound, single photon emission computed tomography (SPECT), or a combination thereof. Multiple first images may be acquired at subsequent time points over a period of time during a dynamic study.

The first image has been reconstructed based on one or more first reconstruction attributes. The first reconstruction attributes may be a spatial resolution, size, reconstruction kernel, slice thickness, de-noising filter, orientation, dimension and/or any other configurable attribute that potentially affect resulting image quality. The selection of reconstruction kernel may be based on the specific clinical application. For example, smooth reconstruction kernels are usually used in brain examinations or liver tumor assessment to reduce image noise and enhance low contrast detectability. Sharper reconstruction kernels are usually used in examinations to assess bony structures due to the clinical requirement of better spatial resolution.

In some implementations, the first image is reconstructed using first reconstruction attributes that are recommended by a standard clinical protocol for user review. In other implementations, the first image is reconstructed using first reconstruction attributes that are suitable for CAD or AI processing and/or clinical review. For example, region identification engine 306 may receive an initial first image from a reconstruction using a lung kernel based on 1.0 mm slice-thickness, even though the standard clinical protocol may require two reconstructions at a slice-thickness of 2.0 mm and using lung and tissue kernels. The first image may also be a scout image, such as a topogram. The scout image is a preliminary image that serves to establish a baseline and is obtained prior to performing the major portion of a particular study.

At 404, region identification engine 306 identifies at least one region of interest (or location or volume of interest) in the first image. It should be appreciated that the terms "location of interest," "region of interest" and "volume of interest" may be used interchangeably herein. The region of interest is any sub-set of the first image that is identified for further study. The region of interest may be characterized by normal anatomy (e.g., organ, anatomical structure) or abnormal anatomy (e.g., lesion or pathology). The region of interest may also be a partition or sub-image of the entire first image. For example, the first image may be partitioned into sub-images of substantially equal sizes. The region of interest may be identified manually, semi-automatically or automatically. Automatic identification of the region of interest may be performed by computer-aided detection, computer-aided diagnosis or other types of artificial intelligence (AI) algorithms. AI algorithms may also be used to localize the region of interest by processing previous clinical reports where the anatomical region of interest has been specified.

Figure 5:
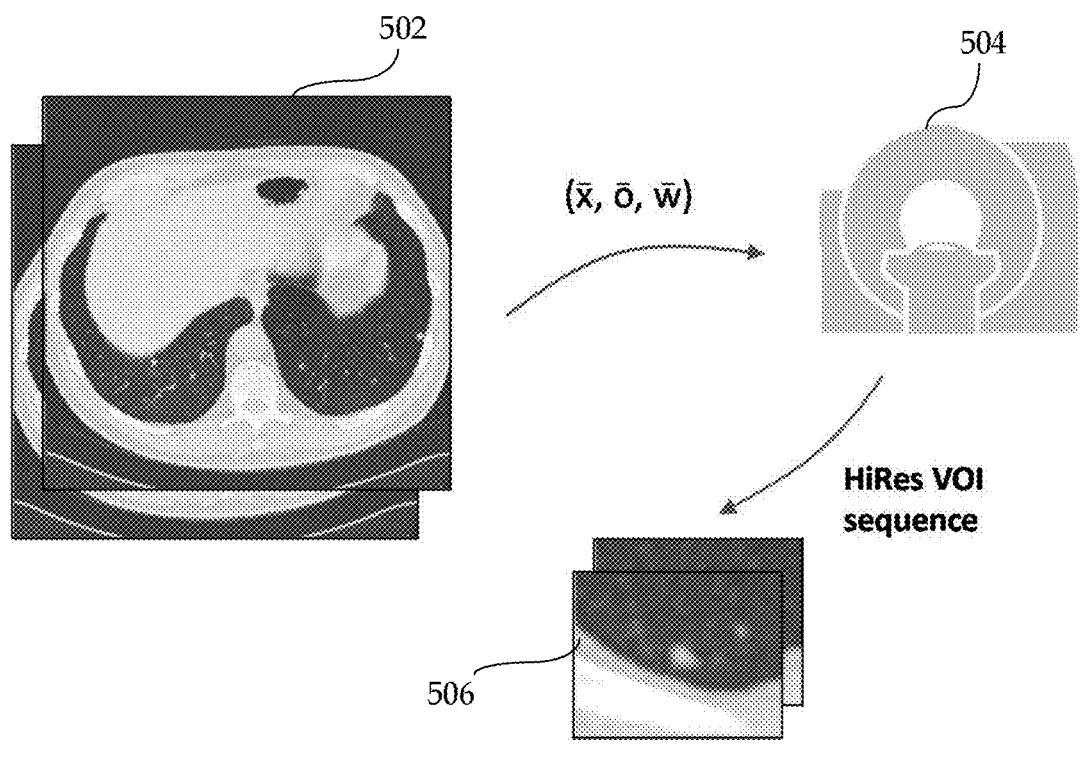
FIG. 5 illustrates an exemplary image reconstruction process based on a user-identified volume of interest.

In some implementations, region identification engine 306 generates a user interface displayed at, e.g., workstation 303, to enable a user (e.g., radiologist, physician, technologist) to select the region of interest on the first image. FIG. 5 illustrates an exemplary image reconstruction process 500 based on a user-identified volume of interest (VOI). Current first images 502 are acquired by image scanner 504 and displayed to a user by a user interface. The user may select a volume of interest by specifying, for example, a location (X), an anatomical orientation (O, if applicable and anatomy based) and/or a dimension (W). In some implementations, the user may select the volume of interest simply by selecting (e.g., via mouse click or screen touch) a location on the first image displayed by a graphical user interface. The user-selected location may be automatically transformed into the acquisition domain (e.g., RAW images for CT scanners) so that a high-resolution image sequence 506 of the VOI may be generated.

In other implementations, region identification engine 306 automatically identifies the region of interest by preprocessing the current first image, processing prior data of clinical reports from similar cases or patients, and/or registering the current first image to an anatomical atlas. Computer-aided Detection (CAD), computer-aided diagnosis or Artificial intelligence (AI) techniques (e.g., convolutional networks, neural networks, random forests) may be employed by region identification engine 306 to perform these operations. The ROI may be propagated from prior data to the current first image by registering the current first image (or sub-regions) with a previously acquired image for the same patient, retrieving or identifying the region of interest (or previous findings) from a prior clinical report or database, and mapping the region of interest via the transformation obtained from the registration to the newly acquired first image.

Figure 6:
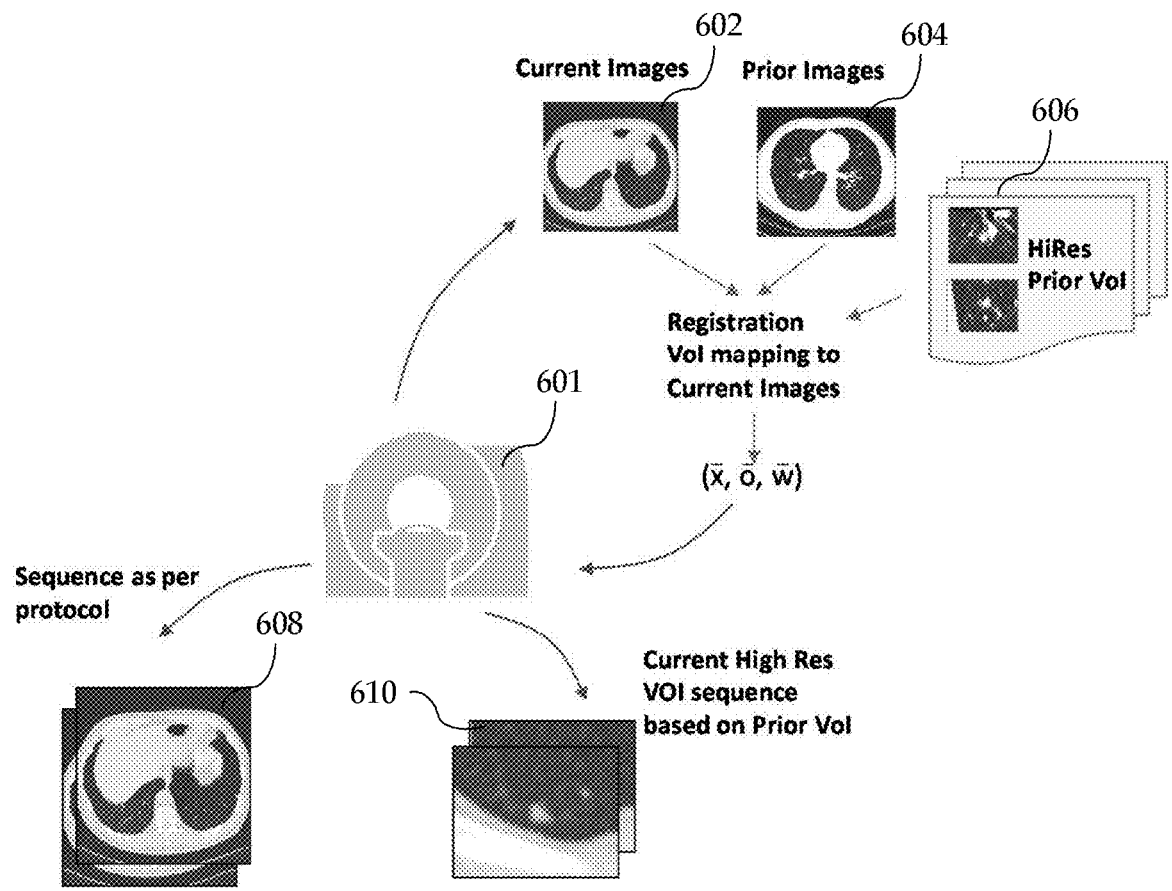
FIG. 6 illustrates an exemplary image reconstruction process based on a volume of interest that is automatically identified from prior images.

FIG. 6 illustrates an exemplary image reconstruction process 600 based on a volume of interest that is automatically identified from prior images. More particularly, as new images 602 are currently acquired by image scanner 601, they are registered to previously acquired prior images 604 and high-resolution prior image volumes 606. The registration establishes a mapping from VOIs identified in the prior images (604, 606) to the currently acquired images 602. Hence, via this mapping, the location of the previously identified VOI(s) may be related to the current acquisition. High resolution image sequences of the VOI 610, as well as image sequences 608 generated according to standard protocol, may then be extracted and made available to the user, together with the current images 602.

Figure 7:
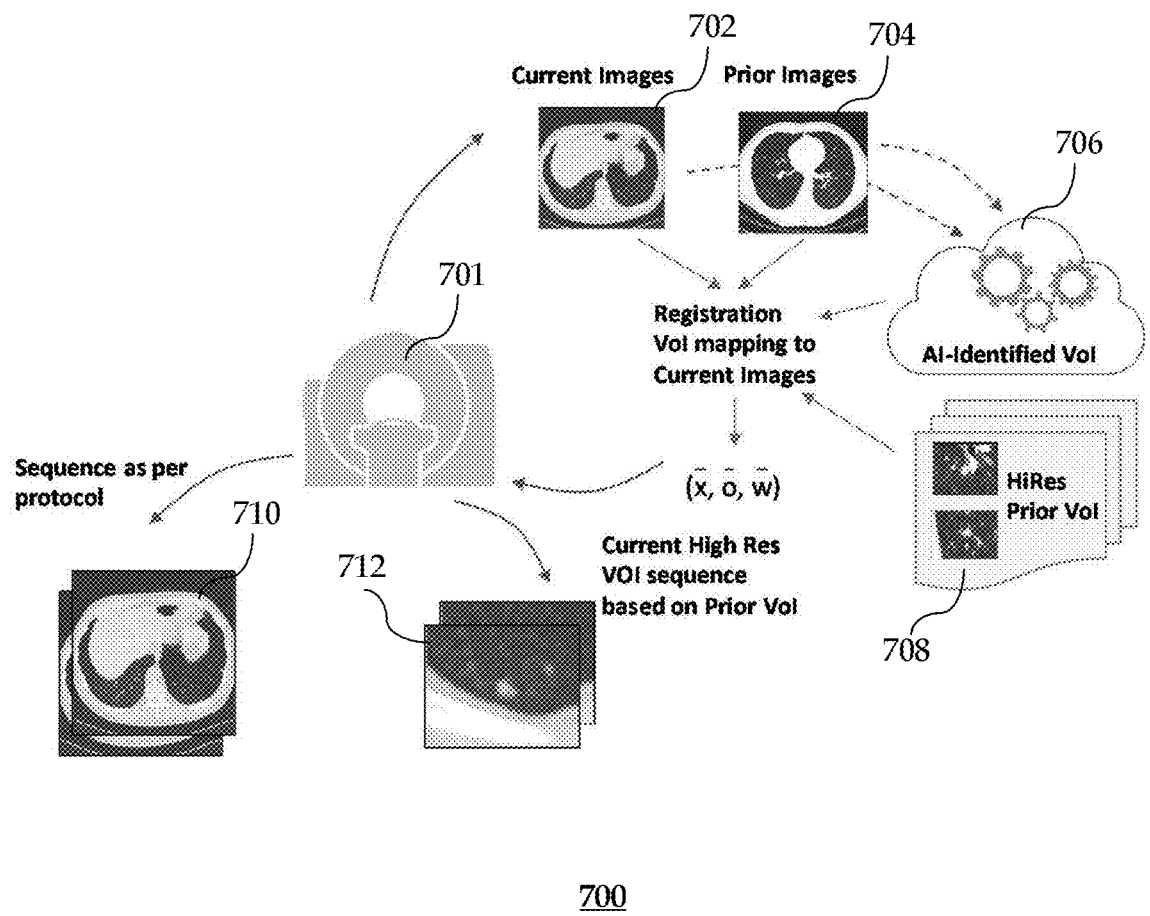
FIG. 7 illustrates another exemplary image reconstruction process based on a volume of interest that is automatically identified from prior images.

FIG. 7 illustrates another exemplary image reconstruction process 700 based on a volume of interest that is automatically identified from prior images. In this example, an artificial intelligence (AI) module implemented in, for example, region identification engine 306, may be used to identify the volume of interest. Such AI-based identification may be performed in addition to using previously identified VOIs in prior images 704 and/or prior high-resolution image volumes 708. More particularly, the previously identified VOIs in prior images 704 and/or prior high-resolution image volumes 708 may be used to train the AI module. The trained AI module may then automatically detect the locations of interest in the first images 702 currently acquired by image scanner 701. For example, a lung CAD technique may be used to identify suspicious nodules or lesions in the current images 702. The volume of interest 706 may then be defined around the detected nodules. An image sequence 710 of the structure of interest may be reconstructed from raw image data acquired by image scanner 701 according to standard protocol. Additionally, a high-resolution image sequence 712 of the identified volume of interest 706 may be selectively reconstructed from the raw image data and reviewed by the user to better assess the clinical value of the findings proposed by the AI module.

Figure 8A:
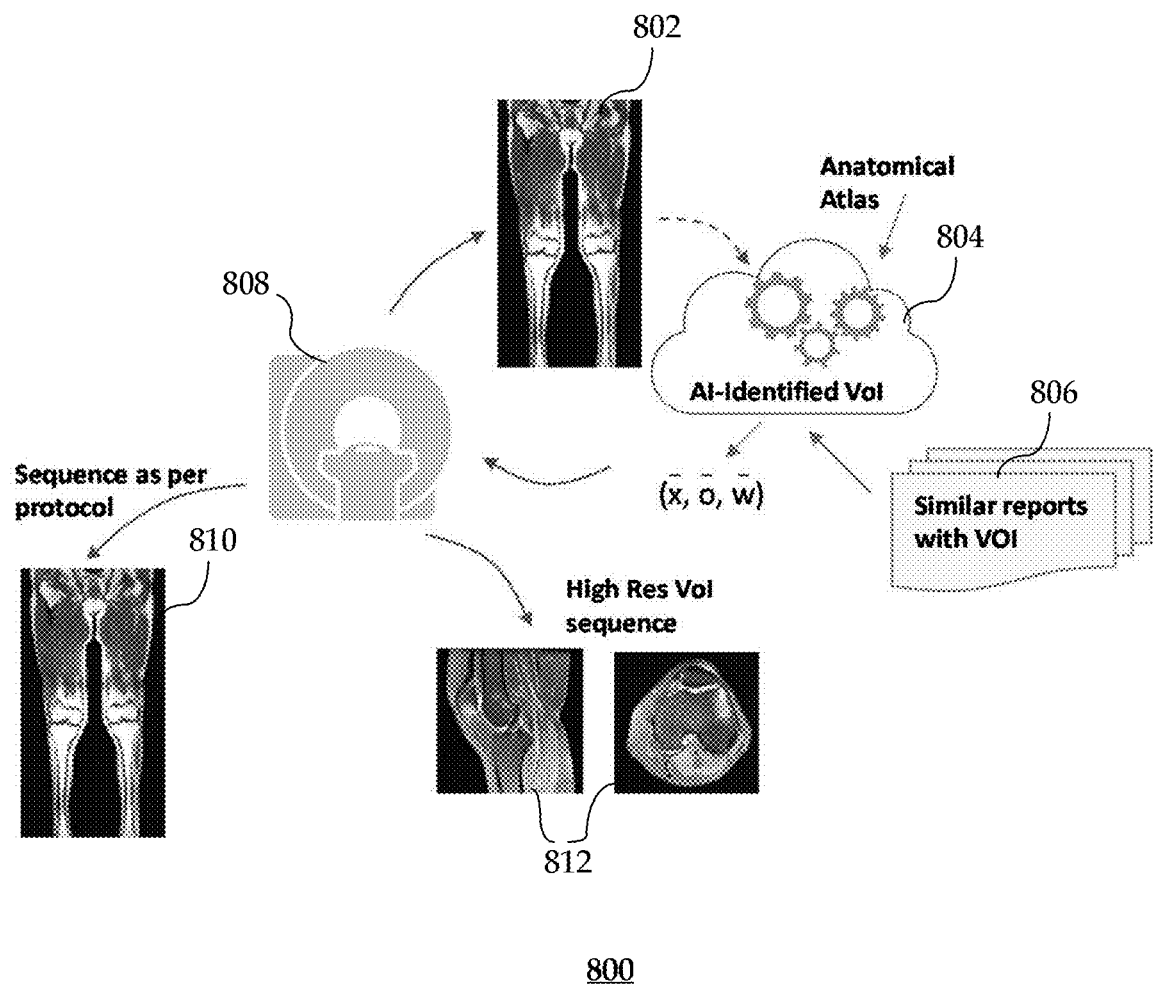
FIG. 8a shows an exemplary image reconstruction process for an application for leg MR image.
Figure 8B:
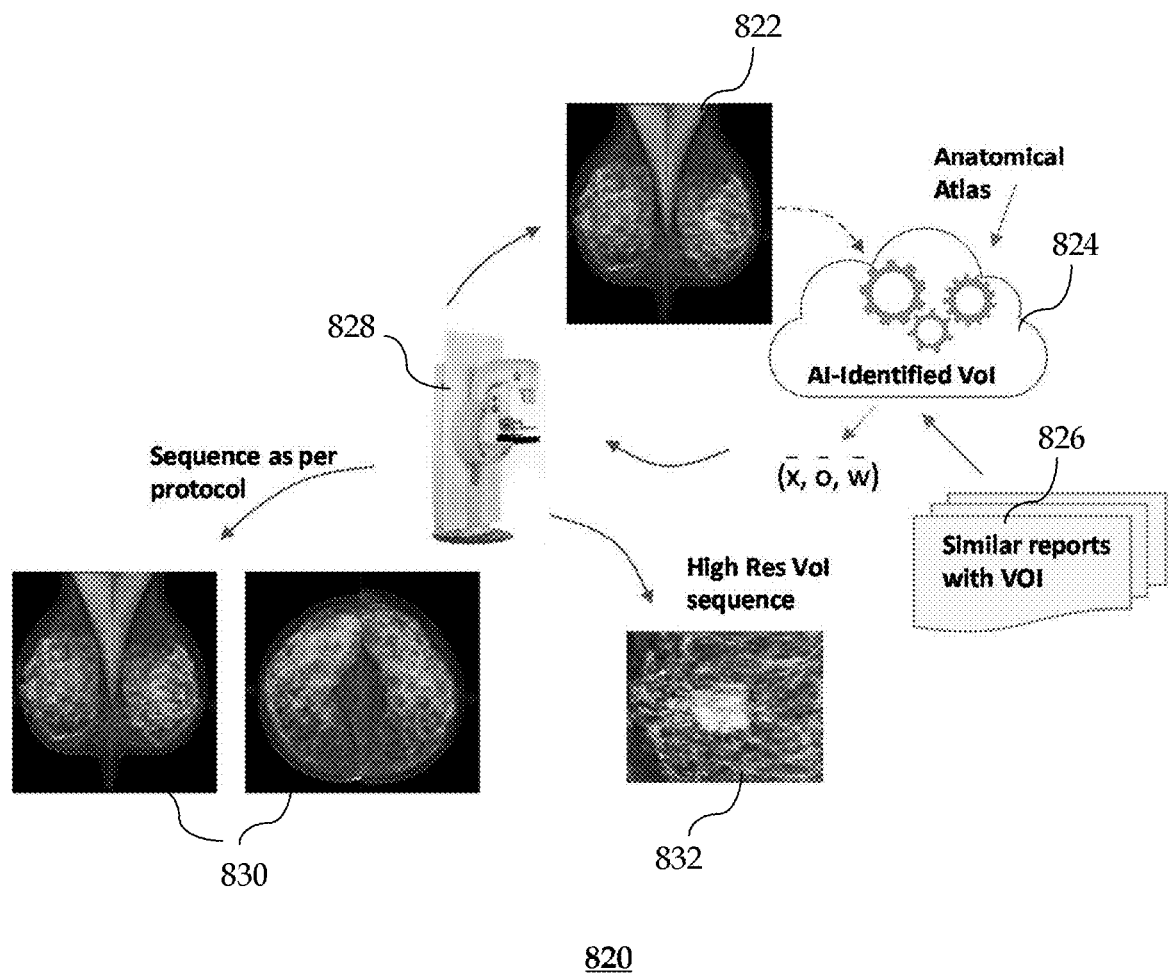
FIG. 8b shows an exemplary image reconstruction process for an application for breast mammogram.

FIGS. 8a and 8b illustrate exemplary applications based on AI-driven identification of regions of interest. More particularly, FIG. 8a shows an exemplary image reconstruction process 800 for an application for leg MR image 802, while FIG. 8b shows an exemplary image reconstruction process 820 for an application for breast mammogram 822.

With reference to FIG. 8a, the application addresses normal anatomy in leg MR image (802) acquired by image scanner 808. Region identification engine 306 automatically reviews the clinical case information (e.g., patient demographics, risk factors) associated with the MR image 802 to determine whether an additional image reconstruction at a higher resolution should be performed. With reference to FIG. 8b, the application addresses abnormal anatomy or potential pathology in the breast mammogram 822 acquired by MR scanner 828. Region identification engine 306 performs image reconstruction with respect to AI-identified volume of interest 824 while taking into account not only clinical case information associated with the specific patient but also similar cases or reports 826 of other patients.

Adaptive reconstruction may be performed for regions (or volumes) of interest that are selected not only by the user (e.g., radiologist, technologist, etc.), but automatically by an AI module in region identification engine 306. The AI module may process the current images (802, 822), compare them with similar prior reports (806, 826) and/or an anatomical atlas to identify volumes of interest (804, 824) for reconstruction at, for example, different levels of resolutions, to generate high-resolution volume sequences (812, 832) and/or image sequences (810, 830) in accordance with standard protocol.

Returning to FIG. 4, at 405, region identification engine 306 generates one or more requests for selective reconstruction of the region of interest based on a second reconstruction attribute. Based on the region of interest identified, the region identification engine 306 may send one or more requests to reconstruction engine 307 for particular reconstructions using at least one second reconstruction attribute. The second reconstruction attribute is different from the first reconstruction attribute used to reconstruct the first image. The second reconstruction attribute may be, for example, a higher spatial resolution or smaller slice thickness. The second reconstruction attribute may be specific to the region of interest identified. For example, if a lung is identified as the region of interest, a lung-specific reconstruction kernel may be specified as the second reconstruction attribute in the request. Other second reconstruction attributes, such as slice thickness, dimension or orientation, may also be specified in the request.

Each region of interest may be associated with its own set of one or more second reconstruction attributes in the request for reconstruction. Requests for additional reconstructions may be based on the candidate locations identified as part of the initial processing. In some implementations, the identification of regions of interest and requests for reconstruction may be performed on multiple images acquired at various different time points spanning the dynamic aspect of a protocol. For example, the protocol may involve acquiring multiple images as part of a single study. Thus, the requests for reconstructions may extend to each of the time points where image scans are performed so as to capture the full dynamic aspect of the study.

Multiple requests for selective reconstruction may be generated for the same location (or region of interest) at the same time point to obtain better computation performance for, e.g., the AI system. For instance, images of the same location with a lung nodule or a liver lesion may be selectively reconstructed with several different kernels. The selectively reconstructed images may then be provided as input to an AI system, to improve the disambiguation of the finding given the additional information.

At 406, reconstruction engine 307 selectively reconstructs one or more second images of the identified region of interest based on at least one second reconstruction attribute. The selective reconstruction by the reconstruction engine 307 may be performed in response to the request received from the region identification engine 306. Reconstruction engine 307 may selectively reconstruct the one or more second images from raw image data acquired by, for example, imaging device 302. The imaging device 302 may acquire the raw image data by using techniques such as high-resolution computed tomography (HRCT), magnetic resonance (MR) imaging, computed tomography (CT), helical CT, X-ray, angiography, positron emission tomography (PET), fluoroscopy, ultrasound, single photon emission computed tomography (SPECT), or a combination thereof. The identified region of interest may be automatically mapped to the acquired raw image data.

Selective reconstruction may be performed using techniques, including but not limited to, iterative reconstruction, filtered back projection, etc. The selective reconstruction may be performed to zoom-in on or target the identified region of interest instead of capturing the entire width or length of the patient's body. The identified region of interest may occupy a substantially larger area or volume in the resulting second image than the first image (i.e. reconstructed at a higher spatial resolution). For instance, if a region of interest occupied a volume 50 mm×50 mm×30 mm in the first image, in the resulting second image, the same region of interest may occupy a volume of 200 mm×200 mm×120 mm. As another example, a first image may include the entire abdomen, while a reconstructed second image may zoom in to show the right kidney. Another iteration of steps 404 and 406 may result in a third set of images that focus on multiple locations of the kidney where lesions are automatically or manually specified.

Figure 9:
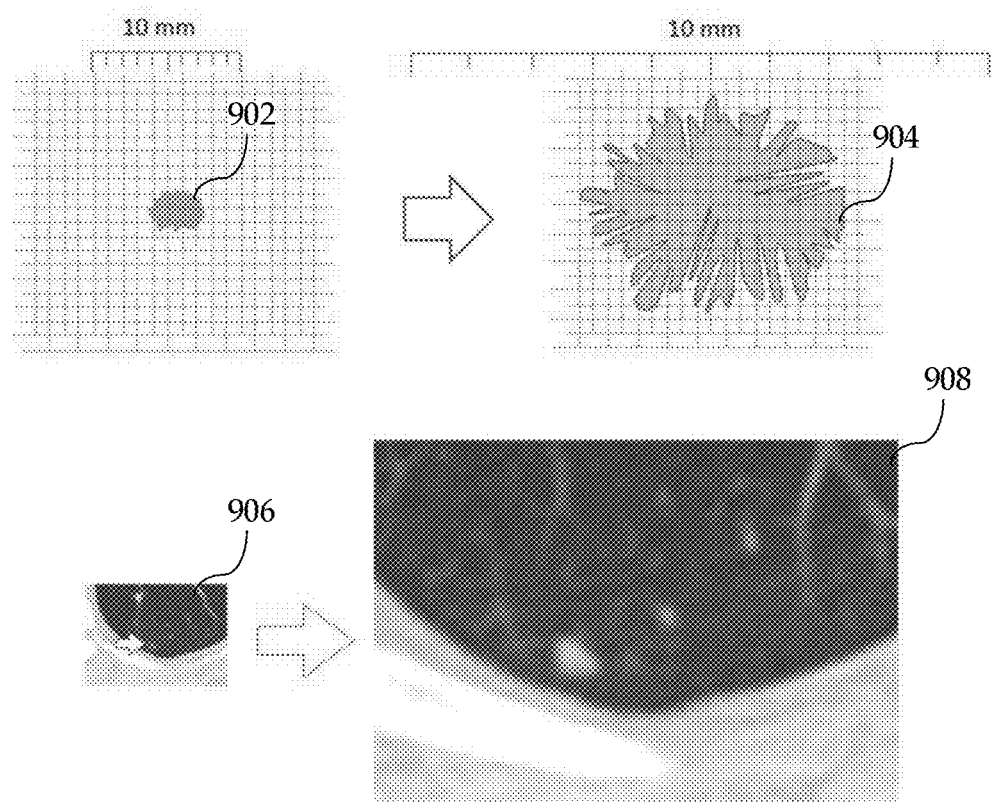
FIG. 9 illustrates the effect of increasing the spatial resolution.

FIG. 9 illustrates the effect of increasing the spatial resolution in the reconstruction. As shown, the structure (e.g., a solitary nodule) 902 on the left measures approximately 3.5 mm×2.5 mm in the original first image 906. When its spatial resolution is increased four times in the reconstructed second image 908, not only can the dimensions of the structure 904 be measured more accurately, its contour can also be better visualized.

For a given resolution, the quantification is subject to the acquisition pose (e.g., translation and/or rotation) of the patient. Quantification effects are observed in areas of the body when motion occurs (e.g., proximal to the diaphragm or heart) or in follow up acquisitions (even after small interval in time with respect priors). When imaged structures are larger, this effect is smaller, yet the digitization effect introduces a methodological variability in the quantification aspect. However, when higher resolutions are used, the borders for structures are more faithfully captured. More faithful border identification and repeatability across image scans translate on contours and volumes which are less sensitive to the digitization aspects and more faithfully capture the underlying structure.

Figure 10:
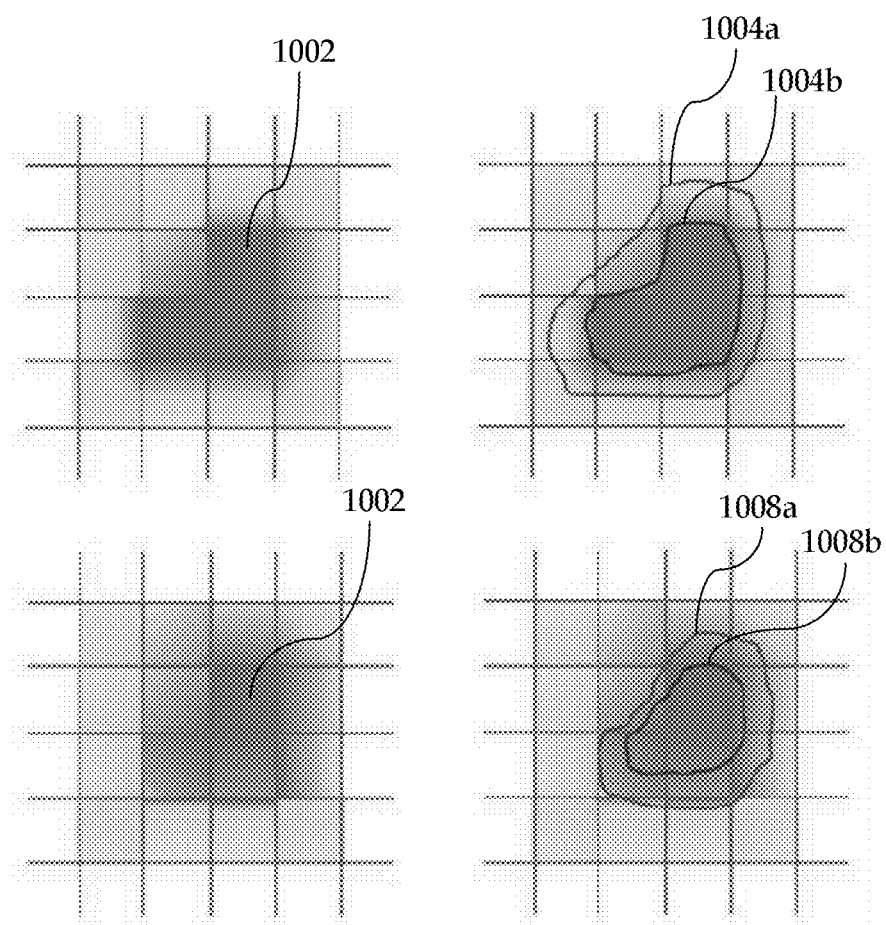
FIG. 10 illustrates the impact of digitization due to pixel grid alignment on contour delineations for the same structure.

FIG. 10 illustrates the impact of digitization due to pixel grid alignment on contour delineations for the same structure. The first row shows the outer and inner potential contours 1004*a-b* of a structure 1002 at a lower image resolution, while the second row shows the outer and inner potential contours 1008*a-b* of the same structure 1002 at a higher image resolution. It can be observed that the variability between the outer and inner contours 1004*a-b* at lower resolution is higher than the variability between the outer and inner contours 1008*a-b* at higher resolution.

Returning to FIG. 4, at 408, reconstruction engine 307 generates results based on the one or more second images. In some implementations, the results include a final sequence of high-resolution second images of the identified regions (or locations) of interest. The results may further include one or more measures that characterize the identified regions of interest, including but not limited to, boundaries (e.g., contours, surfaces) delineating the identified regions of interest, measurements (e.g., width, length, area, volume), attributes, and so forth.

It should be appreciated that the steps 404 and 406 may be repeated in one or iterations to generate a refined list of candidate locations or regions of interest based on intermediate analyses of the reconstructed images. Each of the selectively reconstructed images may be iteratively analyzed to better identify candidate locations or refine the region of interest. In the context of a CAD system, such iterations may greatly improve the confidence and classification of the list of candidates and yield a reduction in false positives.

Figure 11:
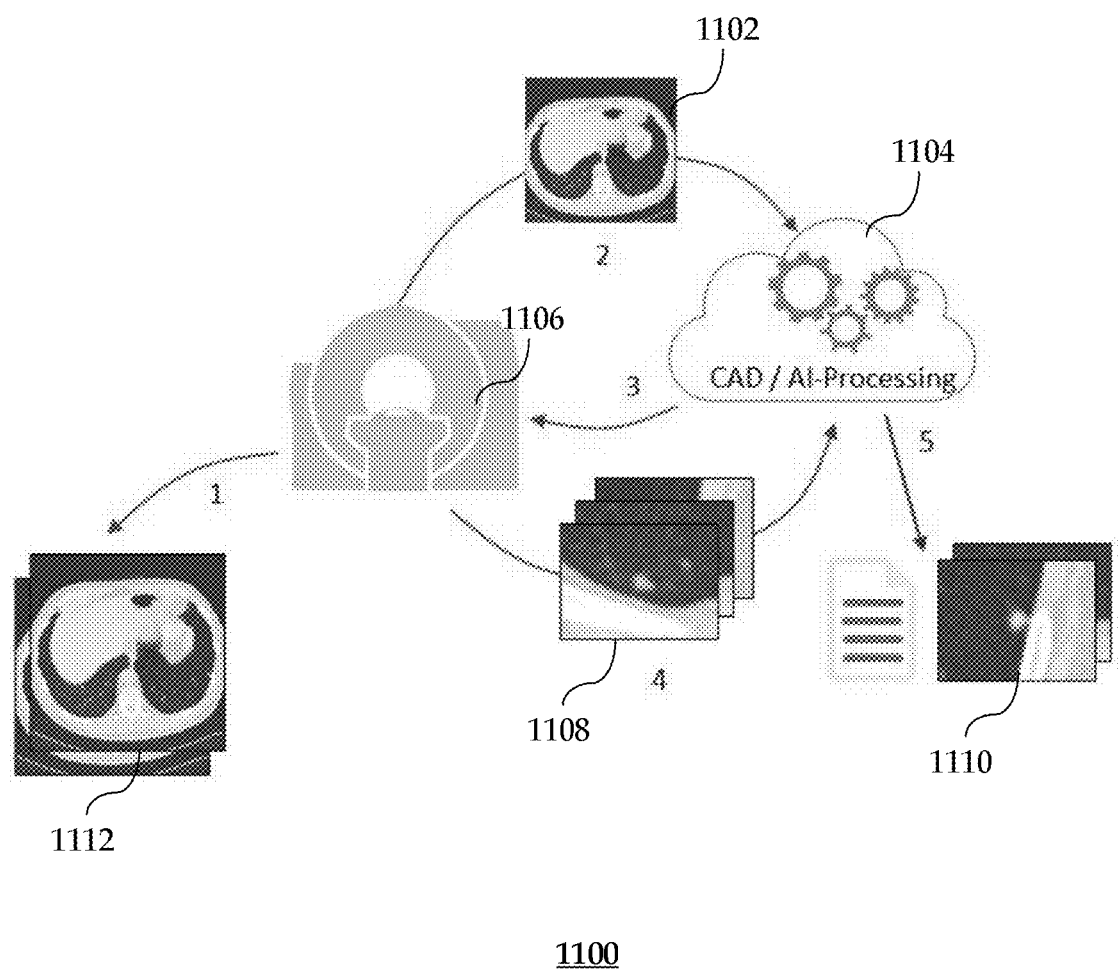
FIG. 11 illustrates an exemplary iterative image reconstruction process based on computer-aided detection (CAD)

FIG. 11 illustrates an exemplary iterative image reconstruction process 1100 based on computer-aided detection (CAD). A basic level of refinement is provided, whereby the initial image 1102 acquired by an image scanner 1106 is processed and locations are identified by the CAD module 1104 for refinement. CAD module 1104 may be implemented in, for example, region identification engine 306.

At step 1, a first image 1102 suitable for CAD or AI processing is initially reconstructed. This may be the same as the one generated using first reconstruction attributes for clinical review of the case or slightly tailored to the type of CAD or AI processing to be performed. While the standard clinical protocol may require two reconstructions at a slice-thickness of 2.0 mm and using lung and tissue kernels to generate images 1112, the CAD module 1104 may have received an initial image 1102 generated by a reconstruction at slice thickness of 1.0 mm and using lung kernel (or multiple images generated using several kernels).

At step 2, the CAD module 1104 may identify one or more locations of interest within the received images 1102 where additional processing may be desired. This may be referred to as a refinement step. These locations of interest may be associated with second reconstruction attributes, such as orientation and dimension (either standard or tailored to the specific finding), as well as other criteria for spatial and kernel reconstructions. Note that any one location of interest may yield multiple reconstructions as per requirement. Therefore, each location of interest may be associated with a set of second reconstruction attributes.

At step 3, upon receiving these locations of interest with specific second reconstruction attributes, reconstruction engine 307 may generate the required sub-volumes 1108 of the locations of interest and make them available to the region identification engine 306.

At step 4, the CAD module 1104 may use the received sub-volumes of the locations of interest to refine the computation of the locations of interest. Following the computation, steps 2, 3 and 4 may be continuously iterated, or step 5 may be performed.

At step 5, the reconstruction engine 307 generates a final list of locations and/or attributes, along with a sequence of high-resolution images 1110.

Figure 12:
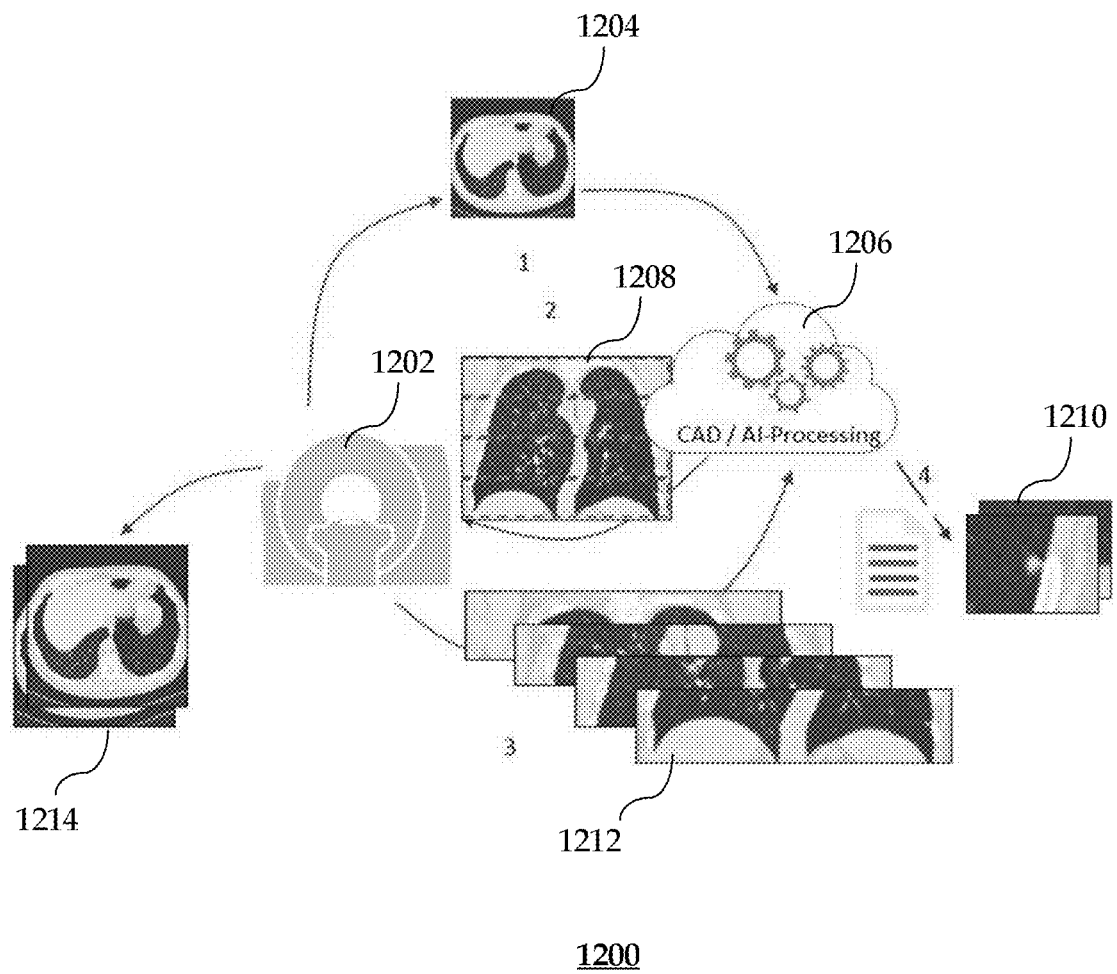
FIG. 12 illustrates another exemplary iterative image reconstruction process.

FIG. 12 illustrates another exemplary iterative image reconstruction process 1200. In the context of a CAD system aimed at detecting specific structures, the initial detection is still bound by the content of information available in the original image. However, in the context of CAD, the detection step may be improved as shown in FIG. 12, whereby the initial identification of regions of interest is improved by interacting with the reconstruction engine 307 and requesting a higher resolution portion of the image. The approach illustrated in FIG. 12 enables not only an initial processing that can be performed at a substantially higher resolution, but it also makes more explicit the parallelizable nature of the processing which can be performed.

At step 1, CAD module 1206 receives an initial reconstructed image (or topogram) 1204 from image scanner 1202 that has been reconstructed using first reconstruction attributes (e.g., lower spatial resolution). Standard clinical protocol may require reconstruction using different reconstruction attributes to generate images 1214.

At step 2, CAD module 1206 identifies regions of interest in the image 1208, which is extracted from initial image 1204. The actual space of image 1208 is partitioned into four sub-images or regions. CAD module 1206 may send, to reconstruction engine 307, a request for reconstruction of the four regions using four sets of second reconstruction attributes (e.g. higher spatial resolution and one or more specific kernels) respectively.

At step 3, reconstruction engine 307 selectively reconstructs each of the regions of interest using the requested second reconstruction attributes to generate reconstructed images 1212. Steps 2 and 3 may then be iterated to further refine the regions of interest based on the selectively reconstructed images 1212 until a stop criterion is satisfied, upon which step 4 is then performed.

At step 4, the reconstruction engine 307 generates a final list of locations and/or attributes, optionally along with a sequence of final reconstructed images 1210.

Figure 13:
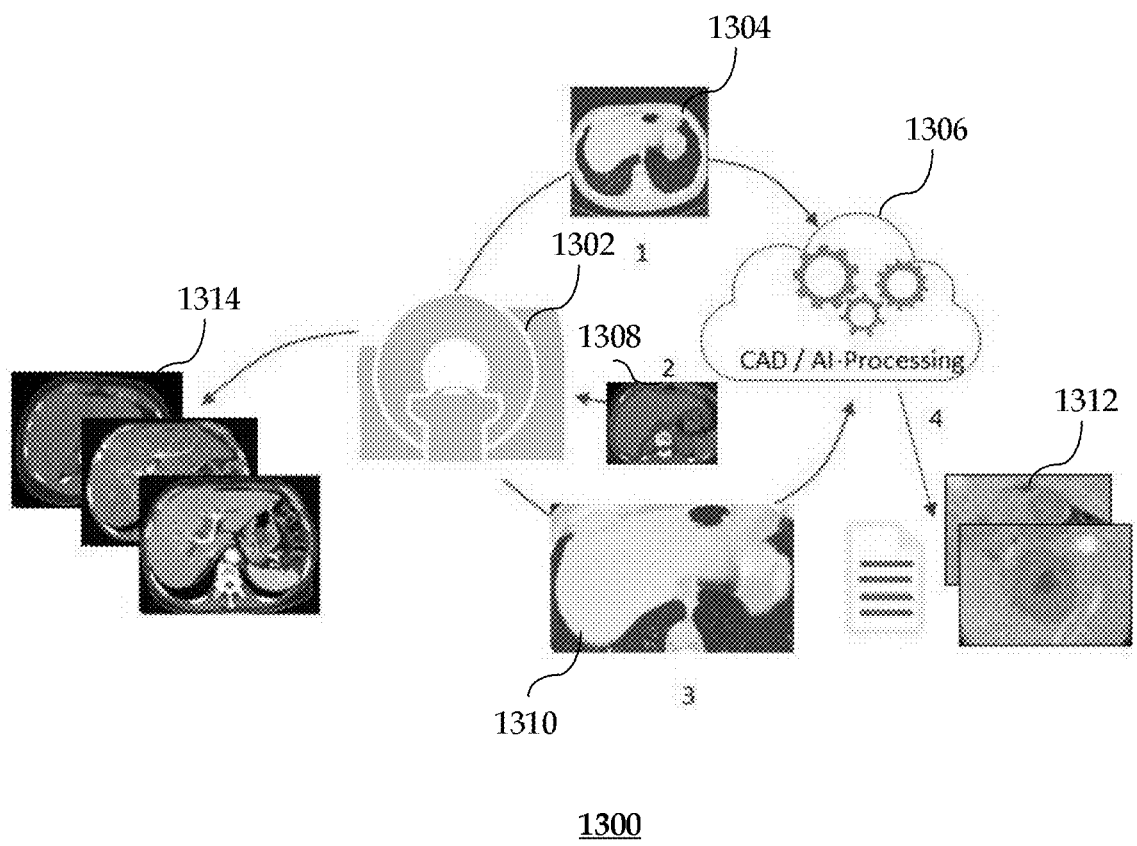
FIG. 13 illustrates yet another exemplary iterative image reconstruction process.

FIG. 13 illustrates yet another exemplary iterative image reconstruction process 1300. The iterative image reconstruction process 1300 involves hierarchical anatomy localization and reconstruction processing focused on specific regions of interest. In this example, the flow 1300 illustrates a liver study performed with the goal of lesion detection and characterization.

At step 1, CAD module 1306 receives an initial reconstructed image 1304 from CT image scanner 1302, possibly at a lower spatial resolution. Standard clinical protocol may require reconstruction using different reconstruction attributes to generate images 1314.

At step 2, CAD module 1306 then identifies a specific anatomical structure or organ (e.g., liver) in image 1308 extracted from initial image 1304 for processing and requests specific reconstructions, rather than partitioning the image space in order to gain more resolution. More particularly, CAD module 1306 may identify the organ by segmentation and request a specific reconstruction aimed at improving the detection and possibly the characterization of potential candidates (e.g., liver lesions).

In other implementations, CAD module 1306 may identify many organs or anatomical structures (e.g., liver, kidneys, aorta, pancreas, etc.) within the CT image 1304 and generate requests for particular reconstructions based on the specific anatomy in question. For example, a liver-specific reconstruction kernel may be specified in the request if a liver is detected in the CT image 1304. In yet other implementations, CAD module 1306 may generate the requests for reconstruction spanning the dynamic aspect of a protocol. More particularly, the protocol may involve multiple CT image acquisitions at different time points as part of a single study (e.g., a profusion study of liver, small bowls, etc.). Requests for selective reconstructions of the region of interest may be generated for multiple CT images that are reconstructed from raw image data acquired by CT image scanner 1302 at different time points so as to capture the full dynamic aspect of the study.

At step 3, reconstruction engine 307 selectively reconstructs images 1310 of the identified anatomical structure using the requested reconstruction attributes. Steps 2 and 3 may then be iterated to further refine the identification (e.g., segmentation) of the anatomical structure or localization of smaller regions of interest (e.g., suspicious candidates) within the anatomical structure based on the reconstructed images 1310 until a stop criterion is satisfied, upon which step 4 is then performed. At step 4, the reconstruction engine 307 generates a final list of locations of candidate lesions and/or attributes, along with a sequence of final selectively reconstructed images 1312.

Figure 14:
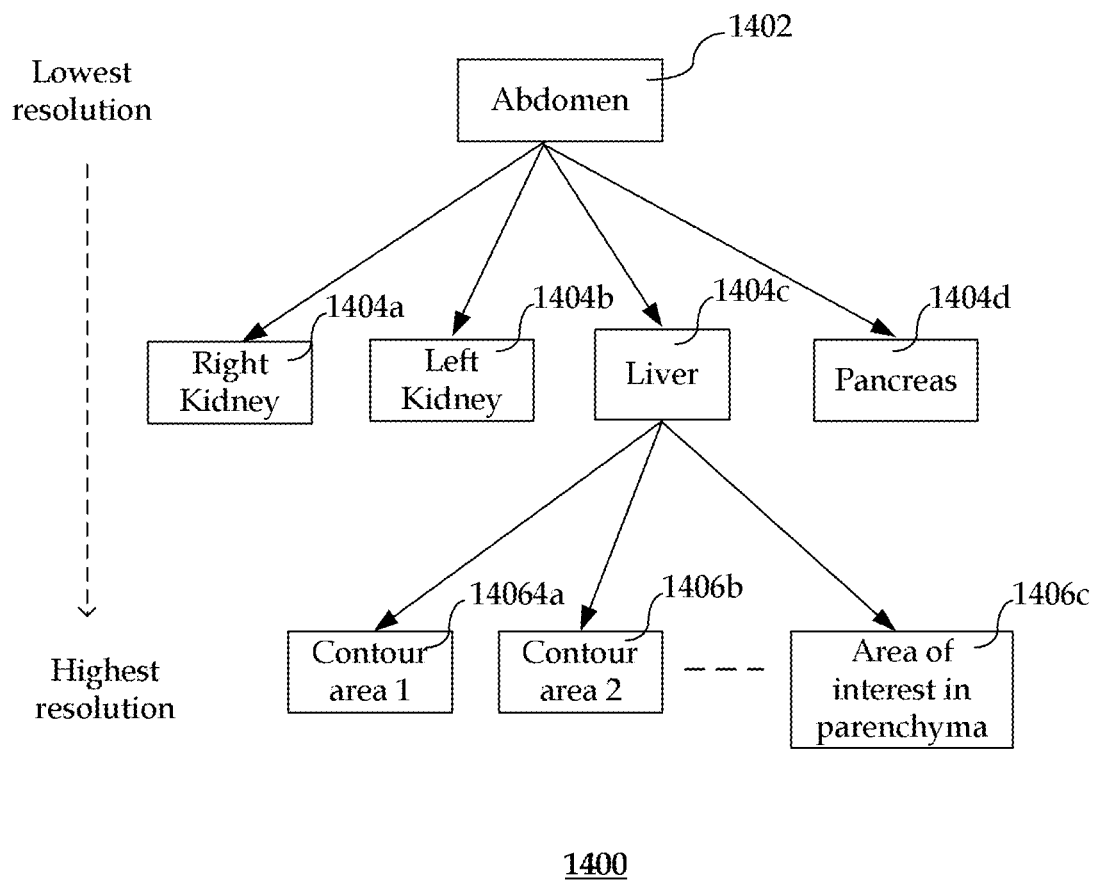
FIG. 14 shows an exemplary tree structure that represents hierarchical localization.

The iterations of steps 2 and 3 may be performed to selectively reconstruct images at successively higher spatial resolutions for hierarchical localization and multi-resolution image representation. FIG. 14 shows an exemplary tree structure 1400 that represents hierarchical localization as well as a hierarchical and adaptive representation of the image data at different levels of resolutions. The nodes of the tree structure 1400 represent the selectively reconstructed images, wherein the top level (root node) image 1402 is selectively reconstructed at the lowest spatial resolution, while the lowest level images 1406*a-c* are selectively reconstructed at the highest spatial resolution. In this example, the structure of interest is the abdomen. It should be appreciated that other anatomical structures may also be localized.

The first iteration of steps 2 and 3 of process 1300 (in FIG. 13) may be performed to identify (or segment) the abdomen in a low resolution initial image 1304 and selectively reconstruct a higher resolution image 1402 of the abdomen. During a second iteration of steps 2 and 3, the image 1402 of the abdomen may be processed to identify (e.g., segment) smaller regions of interest within the abdomen, such as the right kidney, left kidney, liver and pancreas. Higher resolution images 1404*a-d* of these smaller regions of interest may then be selectively reconstructed.

During a third iteration of steps 2 and 3, the image 1404*c* of the liver may be processed to identify (e.g., segment) regions of interest at the contour of the liver, or within the parenchyma. It should be appreciated that other types of regions of interest, such as potential candidates (e.g., lesions), may also be identified within the liver. Higher resolution images 1406*a-c* of these regions of interest may then be selectively reconstructed. The spatial resolution of images 1406*a-c* is higher than the previous level of images 1404*a-d*. Although only three levels are shown, it should be appreciated that further successive iterations may be performed to selectively reconstruct even higher resolution images, such that the spatial resolution of the images increases with each successive iteration. Alternatively, or additionally, the spatial resolution may remain the same but other reconstruction attributes (e.g., slice thickness, kernel) may be different for successive iterations.

Accordingly, the final reconstructed image volume of the structure of interest may be represented and displayed using images of different levels of spatial resolutions (i.e., mixed resolutions). For example, segmentation of certain areas of interest (e.g., at the contour or within the parenchyma) are finer and segmentation for the rest of the anatomical structure is courser.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A system for selective image reconstruction, comprising:
   a non-transitory memory device for storing computer readable program code; and
   a processor in communication with the memory device, the processor being operative with the computer readable program code to perform steps including
   (i) receiving at least one first image that is reconstructed at a first spatial resolution,
   (ii) identifying at least one region of interest in the at least one first image,
   (iii) selectively reconstructing at least one second image of the region of interest at a second spatial resolution that is higher than the first spatial resolution, and
   (iv) generating results based on the at least one second image.

2. The system of claim 1 wherein the first image is reconstructed from raw image data acquired by an imaging device using high-resolution computed tomography (HRCT), magnetic resonance (MR) imaging, computed tomography (CT), helical CT, X-ray, angiography, positron emission tomography (PET), fluoroscopy, ultrasound, single photon emission computed tomography (SPECT), or a combination thereof.

3. The system of claim 1 wherein the second image is selectively reconstructed from raw image data acquired by an imaging device using high-resolution computed tomography (HRCT), magnetic resonance (MR) imaging, computed tomography (CT), helical CT, X-ray, angiography, positron emission tomography (PET), fluoroscopy, ultrasound, single photon emission computed tomography (SPECT), or a combination thereof.

4. The system of claim 1 wherein the processor is further operative with the computer readable program code to refine the at least one region of interest by iterating steps (ii) and (iii) to generate a multi-resolution image representation.

5. A method of selective image reconstruction, comprising:
   (i) receiving at least one region of interest in a first image, wherein the first image is reconstructed based on at least one first reconstruction attribute;
   (ii) generating a request for selective reconstruction of at least one second image of the region of interest, wherein the request includes at least one second reconstruction attribute that is different from the first reconstruction attribute;
   (iii) selectively reconstructing, in response to the request, the at least one second image of the region of interest based on the at least one second reconstruction attribute; and
   (iv) generating results based on the at least one second image.

6. The method of claim 5 further comprises generating a user interface to display the first image and enable a user to select the region of interest from the first image.

7. The method of claim 6 further comprises automatically identifying the region of interest.

8. The method of claim 7 wherein automatically identifying the region of interest comprises propagating the region of interest from a previously acquired image to the first image.

9. The method of claim 7 wherein automatically identifying the region of interest comprises performing an artificial intelligence technique to identify a suspicious abnormality in the first image, wherein generating the request for selective reconstruction comprises generating the request for selective reconstruction of the at least one second image of the suspicious abnormality at a spatial resolution higher than a spatial resolution used to reconstruct the first image.

10. The method of claim 7 wherein automatically identifying the region of interest comprises performing a computer-aided detection technique to identify an anatomical structure in the first image, wherein generating the request for selective reconstruction comprises generating the request for selective reconstruction of the at least one second image of the anatomical structure at a spatial resolution higher than a spatial resolution used to reconstruct the first image.

11. The method of claim 7 wherein automatically identifying the region of interest comprises partitioning the first image into multiple sub-images, wherein generating the request for selective reconstruction comprises generating the request for selective reconstruction of the second images of the multiple sub-images using four sets of second reconstruction attributes.

12. The method of claim 7 wherein generating the request for selective reconstruction of the region of interest comprises reviewing, using an artificial intelligence algorithm, clinical case information associated with the first image to determine whether selective reconstruction should be performed.

13. The method of claim 5 wherein the first and second reconstruction attributes comprise different spatial resolutions, sizes, reconstruction kernels, filters, slice thicknesses, orientations, dimensions, or a combination thereof.

14. The method of claim 5 wherein selectively reconstructing the at least one second image of the region of interest comprises selectively reconstructing the at least one second image at a higher spatial resolution than the first image.

15. The method of claim 5 wherein generating the results based on the at least one second image comprises generating a boundary delineation of the region of interest in the at least one second image.

16. The method of claim 5 wherein receiving the at least one region of interest in the first image comprises receiving the at least one region of interest in multiple first images reconstructed from raw image data acquired at different time points for a single study, wherein generating the request for selective reconstruction comprises generating multiple requests for selective reconstruction of multiple second images of the at least one region of interest.

* * * * *